US010656423B2

United States Patent
Kim et al.

(10) Patent No.: US 10,656,423 B2
(45) Date of Patent: May 19, 2020

(54) HEAD MOUNTED DISPLAY APPARATUS

(71) Applicant: Samsung Electronics Co., Ltd., Suwon-si, Gyeonggi-do (KR)

(72) Inventors: Tae-kyung Kim, Seongnam-si (KR); Jae-woo Ko, Uiwang-si (KR); Soon-seob Han, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 16/504,027

(22) Filed: Jul. 5, 2019

(65) Prior Publication Data

US 2019/0331922 A1 Oct. 31, 2019

Related U.S. Application Data

(63) Continuation of application No. 15/178,978, filed on Jun. 10, 2016, now Pat. No. 10,386,638.

(30) Foreign Application Priority Data

Jan. 19, 2016 (KR) .......................... 10-2016-0006427

(51) Int. Cl.
*G09G 5/00* (2006.01)
*G02B 27/01* (2006.01)
(Continued)

(52) U.S. Cl.
CPC ............ *G02B 27/0172* (2013.01); *A61B 3/10* (2013.01); *A61B 3/1015* (2013.01);
(Continued)

(58) Field of Classification Search
CPC ....... G06T 19/006; G06T 19/00; G06F 3/011; G06F 3/012; G02B 27/017
(Continued)

(56) References Cited

U.S. PATENT DOCUMENTS

| 4,997,269 A | 3/1991 | Cushman |
| 5,278,680 A * | 1/1994 | Karasawa ............... G09F 19/18 348/761 |

(Continued)

FOREIGN PATENT DOCUMENTS

| CN | 101963703 A | 2/2011 |
| DE | 102 19 512 A1 | 11/2003 |

(Continued)

OTHER PUBLICATIONS

Plenoptika, Technology, 2014, Retrieved Apr. 15, 2016, http://plenoptika.com/technology/.

(Continued)

*Primary Examiner* — Gordon G Liu
(74) *Attorney, Agent, or Firm* — Jefferson IP Law, LLP

(57) ABSTRACT

A head mounted display (HMD) apparatus and a display method thereof are provided. The apparatus includes a display configured to provide an image, an active element comprising a plurality of micro-mirrors and configured to reflect the image provided on the display, and a processor configured to detect a user's eyesight and adjust a focal length of the image provided on the display by controlling a gradient of at least some of the plurality of the micro-mirrors based on the detected user's eyesight.

8 Claims, 22 Drawing Sheets

Related U.S. Application Data

(60) Provisional application No. 62/175,627, filed on Jun. 15, 2015.

(51) Int. Cl.

| | | |
|---|---|---|
| *G02B 26/08* | (2006.01) | |
| *A61B 3/10* | (2006.01) | |
| *G02B 27/00* | (2006.01) | |
| *G06T 19/00* | (2011.01) | |
| *G06K 9/00* | (2006.01) | |
| *G02B 27/10* | (2006.01) | |
| *G02B 27/30* | (2006.01) | |
| *G02B 5/30* | (2006.01) | |
| *F21V 8/00* | (2006.01) | |

(52) U.S. Cl.
CPC ..... *G02B 26/0825* (2013.01); *G02B 26/0833* (2013.01); *G02B 27/0093* (2013.01); *G02B 27/1066* (2013.01); *G06K 9/00604* (2013.01); *G06T 19/006* (2013.01); *G02B 5/30* (2013.01); *G02B 6/0056* (2013.01); *G02B 27/30* (2013.01); *G02B 2027/011* (2013.01); *G02B 2027/014* (2013.01); *G02B 2027/0123* (2013.01); *G02B 2027/0127* (2013.01); *G02B 2027/0178* (2013.01)

(58) Field of Classification Search
USPC ........................................................ 345/633
See application file for complete search history.

(56) References Cited

U.S. PATENT DOCUMENTS

| | | | |
|---|---|---|---|
| 5,959,780 A | 9/1999 | Togino et al. | |
| 5,982,343 A | 11/1999 | Iba et al. | |
| 6,722,767 B2 | 4/2004 | Dick et al. | |
| 6,977,777 B1* | 12/2005 | Wick | G02B 17/0694 |
| | | | 359/677 |
| 7,233,422 B2* | 6/2007 | Endo | G02B 27/0172 |
| | | | 345/32 |
| 7,486,341 B2 | 2/2009 | Hong et al. | |
| 7,764,413 B2 | 7/2010 | Levola | |
| 8,836,720 B2 | 9/2014 | Oyama et al. | |
| 8,934,160 B2 | 1/2015 | Sun | |
| 9,279,984 B2 | 3/2016 | Aiki et al. | |
| 2006/0228073 A1 | 10/2006 | Mukawa et al. | |
| 2006/0232498 A1 | 10/2006 | Seo et al. | |
| 2009/0195751 A1 | 8/2009 | Hillis et al. | |
| 2010/0091027 A1 | 4/2010 | Oyama et al. | |
| 2010/0169108 A1 | 7/2010 | Karkanias et al. | |
| 2011/0019250 A1 | 1/2011 | Aiki et al. | |
| 2011/0211239 A1 | 9/2011 | Mukawa et al. | |
| 2012/0162549 A1 | 6/2012 | Gao et al. | |
| 2013/0258486 A1 | 10/2013 | Ionescu et al. | |
| 2014/0092461 A1 | 4/2014 | Spitzer et al. | |
| 2014/0126056 A1 | 5/2014 | Amitai et al. | |
| 2014/0126057 A1* | 5/2014 | Amitai | H04N 13/344 |
| | | | 359/489.08 |
| 2014/0160588 A1 | 6/2014 | Aiki et al. | |
| 2014/0327604 A1 | 11/2014 | Oyama et al. | |
| 2014/0375790 A1 | 12/2014 | Robbins et al. | |
| 2015/0067580 A1 | 3/2015 | Um et al. | |
| 2015/0138048 A1 | 5/2015 | Park | |
| 2016/0066780 A1 | 3/2016 | Pamplona et al. | |
| 2016/0143529 A1 | 5/2016 | Myashita et al. | |

FOREIGN PATENT DOCUMENTS

| | | |
|---|---|---|
| JP | 9-127458 A | 5/1997 |
| JP | 2000-89157 A | 3/2000 |
| JP | 5341462 B2 | 11/2013 |
| KR | 10-2007-0021154 A | 2/2007 |
| KR | 10-2015-0009852 A | 1/2015 |
| WO | 2012-009115 A1 | 1/2012 |
| WO | 2014-209431 A1 | 12/2014 |

OTHER PUBLICATIONS

Berthouzoz et al., Resolution Enhancement by Vibrating Displays, ACM Transactions on Graphics, pp. 1-13, ACM, Inc., New York, NY, USA.

Berthouzoz, Resolution Enhancement by Vibrating Displays, ACM TOG, Nov. 27, 2011, YouTube, https://www.youtube.com/watch?v=OYY0Zi6pT8I.

European Office Action dated Mar. 9, 2018, issued in European Application No. 16174393.5.

Chinese Office Action dated Jan. 16, 2020, issued in Chinese Application No. 201610424539.9.

Taiwanese Office Action dated Mar. 19, 2020, issued in Taiwanese Application No. 105116945.

* cited by examiner

HEAD MOUNTED DISPLAY APPARATUS

CROSS-REFERENCE TO RELATED APPLICATION(S)

This application is a continuation application of prior application Ser. No. 15/178,978, filed on Jun. 10, 2016, and was based on and claimed priority under 35 U.S.C. § 119(e) of a U.S. Provisional application Ser. No. 62/175,627, filed on Jun. 15, 2015, in the U.S. Patent and Trademark Office, and under 35 U.S.C. § 119(a) of a Korean patent application number 10-2016-0006427, filed on Jan. 19, 2016, in the Korean Intellectual Property Office, the disclosure of which is incorporated by reference herein in its entirety.

TECHNICAL FIELD

The present disclosure relates to a head mounted display apparatus. More specifically, the present disclosure relates to a display apparatus configured to measure the user eyesight by using an active element and correct the eyesight by adjusting a focal point.

BACKGROUND

In a head mounted display (HMD), the optics display collimates, magnifies, and relays an image source. "Collimating" an image indicates that a virtual image is generated and accurately aligned to appear a few inches farther from a user's face. "Magnifying" an image indicates that an image is made to appear larger than the actual size of the image. "Relaying" an image source indicates that the virtual reality image is generated away from the user's face and the image source.

Recently, the HMD has required more elaborate and sophisticated technologies as it is used to display virtual reality (VR) and augmented reality (AR). Because HMD is a display apparatus used closest to the user's eye, a technology which can reduce eye fatigue is needed.

One of related art methods for measuring and correcting the eyesight of the user involves correcting the eyesight by adjusting the position of the lenses constituting the optics within the HMD to control the optical path length. Further, there also is an eyesight correcting method that involves adjusting the position of the displays constituting the optics within the HMD to control the optical path length.

However, the technologies of the related art have shortcomings such that the precise eyesight measurement, correction of the eyesight of the left and right eyes respectively, and correcting astigmatism cannot be performed. Further, when a plurality of users share a same HMD, the users may experience the inconvenience of needing to re-adjust the eyesight measurements whenever users are changed.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a display apparatus that can reduce the size of a head mounted display (HMD) apparatus by using an active element that varies a focal length, and that corrects the user eyesight automatically based on information stored based on measurements of the eyesight of left and right eyes and in association with user information, and a control method thereof. Accordingly, the eye fatigue of a user of HMD can be reduced.

Another aspect of the present disclosure is to provide a high definition display screen to a user by using such an active element.

In accordance with an aspect of the present disclosure, an HMD apparatus is provided. The apparatus includes a display configured to provide an image, an active element comprising a plurality of micro-mirrors and configured to reflect the image provided on the display, and a processor configured to detect a user's eyesight and adjust a focal length of the image provided on the display by controlling a gradient of at least some of the plurality of the micro-mirrors based on the detected user's eyesight.

The processor may generate a mask pattern on the active element such that only a certain area of an optical ray for the eyesight measurement emitted from the display is formed as an image on a user's retina, and detect the eyesight by varying an optical power of the active element.

The processor may correct the user eyesight by adjusting an optical power of the active element based on the detected user's eyesight.

The processor may vary a focal point of a virtual reality image displayed on the display at a designated time, or vary a focal length of the virtual reality image by estimating an object position of the virtual reality image displayed on the display with image recognition and varying a focal point of the image.

The processor may adjust a focal point of each layer of the virtual reality image by varying power of the active element proportionally to an object distance of the virtual reality image, and when the user is myopic (nearsighted), expand an eyesight adjustment range of the user by designating an offset on the power of a lens such that the power of the active element is varied.

The processor use high-speed tilting to drive the active element such that the resolution of the display is expanded.

The active element may be disposed in a vertical direction with regard to the display and an optical path.

The HMD apparatus may additionally include a memory configured to store the detected eyesight information and the user's biometric information.

The HMD apparatus may additionally include a plurality of polarizers. The HMD apparatus may obtain a virtual reality image with a first polarizer disposed between the active element and the lens, a second polarizer disposed between a lens mirror and a front surface of a second polarized beam splitter, and a third polarizer disposed perpendicularly to the second polarizer, parallel with the active element, and disposed on a side surface of the second polarized beam splitter.

The first polarizer and the second polarizer may be quarter wave plates, and the third polarizer may be a half wave plate.

The HMD apparatus may additionally include a collimating lens configured to generate the optical ray emitted from the display into a parallel ray, an active element configured to converge or diverge the optical ray emitted from the lens, a first diffraction element configured to diffract the optical ray emitted from the active element, a quarter wave plate disposed between the first diffraction element and the active element and configured to change the polarized state, a light guide configured to light-guide the diffracted optical ray with total reflection, and a second diffraction element configured to emit the optical ray to a user with the diffraction.

The first diffraction element may pass a first linear polarized optical ray emitted from the display and diffract a second linear polarized optical ray perpendicular to the first linear polarized optical ray.

The HMD apparatus may adjust a focal point of an augmented reality image by disposing the first diffraction element to be parallel with the active element, disposing the second diffraction element to be parallel with the user's eye, and disposing an optical axis of the active element by a designated angle with respect to an optical axis of the user's eye.

According to an embodiment of the present disclosure, a display method of an HMD apparatus is provided. The method includes detecting eyesight information of a user by using an active element comprising a plurality of micro-mirrors, storing the detected user's eyesight information with user's information, and when the user is recognized based on the user's information, adjusting a focal length of an image provided to a display by controlling a gradient of at least some of the plurality of micro-mirrors based on the detected user's eyesight information.

The detecting may include generating a mask pattern configured so that only a certain area of the optical ray emitted from the display is formed on a center of the active element for the eyesight measurement and the areas can be formed as an image on the user retina, and measuring the eyesight by varying an optical power of the active element.

The display method may additionally include correcting the eyesight of the user by adjusting the optical power of the user based on the eyesight detected from the active element.

The adjusting of the focal length further may include one of varying a focal point of a virtual reality image displayed on the display at a designated time and varying a focal length of the virtual reality image by estimating an object position within the virtual reality image displayed on the display through the image recognition and varying a focal point of the image.

The display method may additionally include adjusting a focal point of each layer of a virtual reality image by varying the power of the active element proportionally to an object distance within the virtual reality image.

The display method may additionally include, when a user is myopic, expanding an eyesight adjustment range of the user by designating an offset on the power of a lens such that the power of the active element is varied.

The display method may additionally include using high-speed tilting to drive the active element so as to expand a resolution of the display.

As described above, the HMD apparatus according to various embodiments of the present disclosure may provide the optimized image for a user by measuring the user eyesight with the active element. Further, the HMD apparatus may be miniaturized by using the active element and provide a high definition display screen to a user.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, like reference numerals will be understood to refer to like parts, components, and structures.

DETAILED DESCRIPTION

Figure 1:
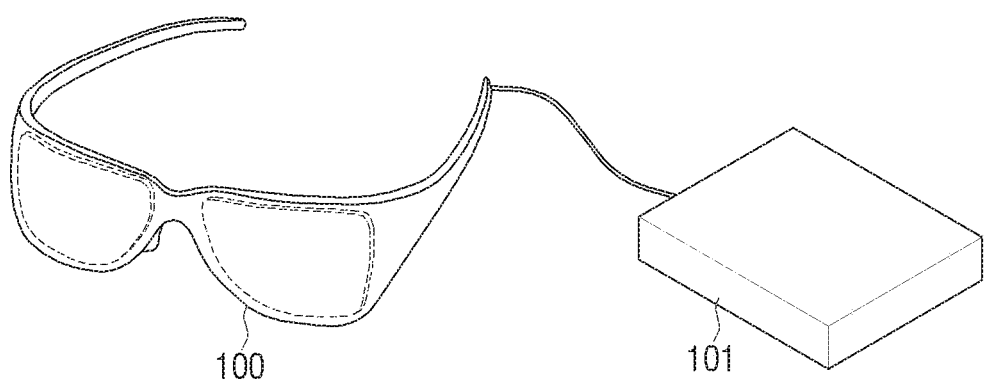
FIG. 1 is a diagram illustrating a general configuration of a head mounted display (HMD) according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments of the present disclosure described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Further, the suffixes "-er (-r)" attached to names of the elements used herein are given or mixed solely in consideration of an ease of writing the description, and therefore, these do not impart any distinguishing meanings or roles from one another.

Further, expressions including ordinal numbers such as "first", "second", and so on as used herein may be used for describing a variety of elements, but the elements should not be limited by such expressions. The expressions mentioned above are used with a sole purpose of distinguishing one element from another. For example, without departing from the scope of the present disclosure, a "first element" may be named a "second element", or similarly, the "second element" may be named the "first element".

Certain embodiments of the present disclosure will now be described in greater detail with reference to the accompanying drawings.

In the following description, same drawing reference numerals are used for the same elements even in different drawings. The matters defined in the description, such as detailed construction and elements, are provided to assist in a comprehensive understanding of the present disclosure. Accordingly, it is apparent that the various embodiments of the present disclosure can be carried out without those specifically defined matters.

Referring to the attached drawings, the present disclosure will be described in detail below.

FIG. 1 is a diagram illustrating a general configuration of a head mounted display (HMD) according to an embodiment of the present disclosure.

Referring to FIG. 1, the HMD 100 may be a display apparatus in binocular form. However, the present disclosure is not limited thereto, and accordingly, the HMD 100 may be mounted on the head or may include a thin and light configuration like general eyeglasses.

According to an embodiment of the present disclosure, the HMD 100 may include a display displaying an image to the left and right eyes, an optical section (not illustrated) that can measure the user's eyesight, and a controller 101. The controller 101 may be configured externally from the HMD 100 or internally within the HMD 100. A processor 220 of FIG. 2A may perform a function of the controller 101. The optical section will be specifically explained in FIG. 2B.

The controller 101 may correct the user's eyesight by adjusting the optical power based on the user's eyesight measured in the optical section. Further, the controller 101 may store the measured user's eyesight in a memory (not illustrated), and control the optical section to measure the eyesight based on the stored user information.

When the controller 101 is configured externally from the HMD 100, the HMD 100 may perform the communication with the controller 101, and the controller 101 may perform the communication such that the HMD 100 can receive an image from an image processing apparatus (not illustrated). The HMD 100 and the controller 101 may be configured to perform the communication wired or wirelessly.

Further, an embodiment of the present disclosure can be applied to all display apparatuses having optics that can measure and correct the user's eyesight in a display apparatus as well as the HMD 100.

Figure 2A:
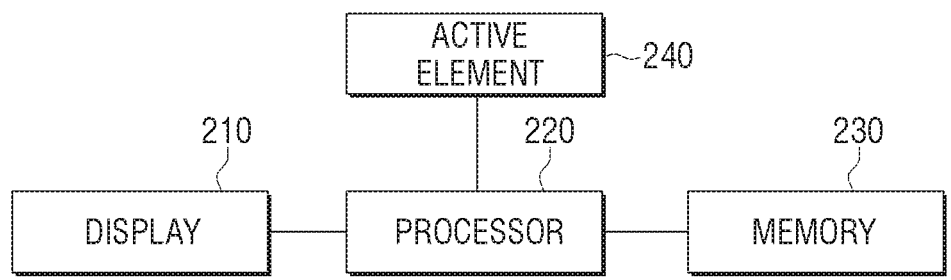
FIG. 2A is a block diagram briefly illustrating configuration of an HMD according to an embodiment of the present disclosure.

FIG. 2A is a block diagram briefly illustrating a configuration of an HMD according to an embodiment of the present disclosure.

Referring to FIG. 2A, the HMD 100 may include the display 210, the processor 220, the memory 230, and an active element 240.

The display 210 may provide images, and display corrected images suitable for the user's eyesight based on the left and right eye eyesight of a user which is measured by using the active element 240, and the user information stored in the memory 230 according to a controlling command of the processor 220.

Further, the display 210 may be implemented as various forms such as a liquid crystal display (LCD), an organic light emitting diode (OLED), a flexible display, a three-dimensional (3D) display, and so on. The display 210 may be configured as a touch screen and used as an inputting device for receiving the inputting of a user touch command as well as an outputting device.

The memory 230 may store the user's eyesight information and biometric information generated by the processor 220. Further, the memory 230 may store the corrected eyesight information of a user. The memory 230 may store programs, calculation parameters, and user instructions used in the processor 220. For example, the memory 220 may include at least one of a hard disk, a multimedia card, a flash memory, a micro secure digital (SD) card, or extreme digital (XD) card. Further, the memory 230 may be random access memory (RAM) or read only memory (ROM) within the processor 220.

The active element 240 may modify a focal point by adjusting the optical power of a user, and include a deformable mirror in which a gradient can be varied. The active element 240 may include a plurality of micro-mirrors, and reflect the image provided form the display 210. Explained below is an embodiment of the present disclosure in which a micro-electromechanical systems (MEMS) mirror including the micro-mirrors is used as active element 240. The active element 240 will be specifically explained by referring to FIGS. 6A and 6B.

The processor 220 may control the active element 240 to detect the user's eyesight, and adjust a focal length of the image provided from the display 210 by controlling a gradient of at least some of a plurality of the micro-mirrors in the active element 240 based on the detected user's eyesight.

The processor 220 may control the display 210 to generate an eyesight measuring optical ray, and control the active element 240 such that the eyesight measuring optical ray can be formed as an image on the retina of a user through at least one of a plurality of the micro-mirrors in the active element 240. Further, the processor 220 may register the user eyesight information in the memory 230 based on the detected information from the active element 240 at the time point when the image is formed on the user's retina.

The processor 220 may generate a mask pattern on the active element 240 such that some areas among the optical ray for measuring the eyesight emitted from the display 220 are formed as an image on the user retina, and detect the eyesight by varying the optical power of the active element 240. Further, the processor 220 may correct the user's eyesight by adjusting the optical power of the active element 240 based on the detected eyesight.

Further, the processor 220 may modify a focal point of the virtual reality image displayed on the display 210 at a designated time. Further, the processor 220 may modify a focal length of the virtual reality image by estimating the object position of the virtual reality image displayed on the display 210 with the image recognition and varying a focal point of the image.

Further, the processor 220 may adjust a focal point of a layer of the virtual reality image by varying the power of the active element so as to be proportional to a distance of the object of the virtual reality image. Further, when a user of the HMD 100 is myopic, the processor 220 may designate an offset on the power of a lens, and expand the eyesight adjustment range of a user as the power of the active element 240 is varied.

The processor 220 may be configured to measure the user's eyesight by receiving a user command and varying the gradient of the micro-mirrors of the active element. For example, the processor 220 may be configured to modify the gradient of the micro-mirrors of the active element by a user through a user interface (UI) for the eyesight measurement or menu buttons. For example, the processor 220 may receive a command to adjust eyesight and a command to measure eyesight from a user through a touch input or a drag input to a touch screen of the HMD 100. Also, the processor 220 may receive a command to adjust eyesight and a command to measure eyesight from the user through a user manipulation command such as a wheel button provided in the HMD 100.

The HMD 100 may include a communicator (not illustrated). The communicator may perform the wired/wireless data communication with an external electronic device. When performing the data communication with an external electronic device according to the wireless communication method, the communicator may include at least one of a Wi-Fi direct communication module, a Bluetooth (BT) module, an infrared data association (IrDA) module, a near field communication (NFC) module, a ZigBee module, a cellular communication module, a 3rd generation (3G) mobile communication module, a 4th generation (4G) mobile communication module, and a long term evolution (LTE) communication module.

Herein, when performing the data communication with an external electronic device according to the wired communication method, the communicator may include an interface module such as a universal serial bus (USB). Through the interface module, the communicator may transmit or receive the image data or transmit or receive the firmware data to perform the firmware upgrading while physically connected to an external terminal such as a personal computer (PC).

Through the above process, the HMD 100 according to an embodiment of the present disclosure may provide an optimized image for a user by measuring the user's eyesight with the active element 240.

Figure 2B:
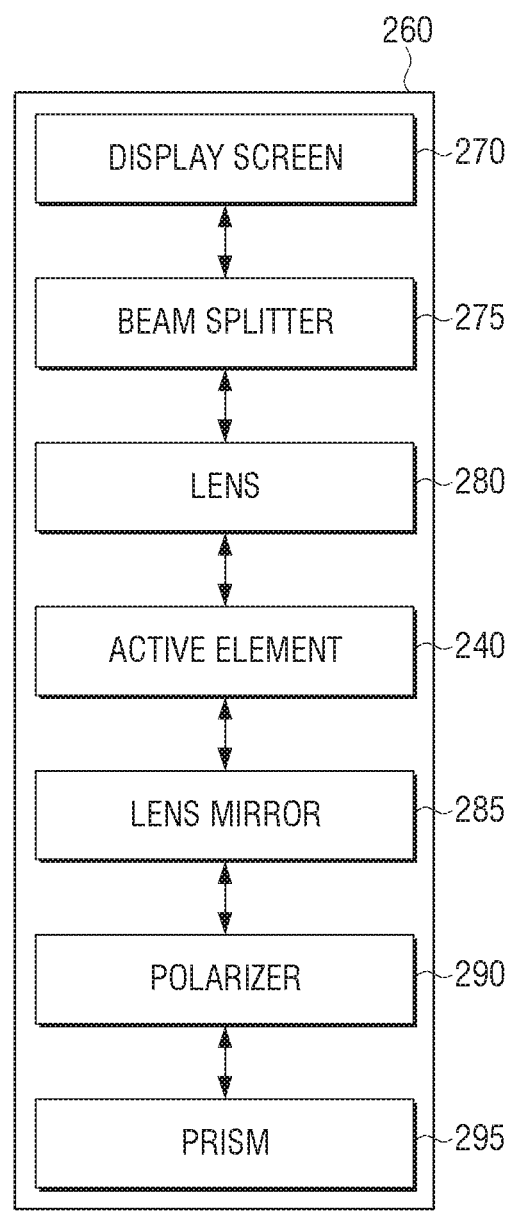
FIG. 2B is a block diagram briefly illustrating a configuration of an optical section in an HMD according to an embodiment of the present disclosure.

FIG. 2B is a block diagram briefly illustrating configuration of an optical section of an HMD according to an embodiment of the present disclosure.

Referring to FIG. 2B, the optical section 260 may include the active element 240, a display screen 270, a beam splitter 275, the lens 280, a lens mirror 285, a plurality of polarizers 290 (quarter wave plates or half wave plates), and a prism 295. Units constituting the optical section 260 are not limited to the above; other new units may be further included. The features of each unit will be specifically explained by referring to FIG. 5.

The display screen 270 may generate the optical ray on the left and right eyes of the HMD 100. The display screen 270 may be planar or curved. The display screen 270 may include indicator optics. The display screen 270 may be included one on each of the left and right eyes of the HMD 100, or included two on each of the left and right eyes of the HMD 100. Explained below is an embodiment of the present disclosure in which the display screen 270 is included one on each of the left and right eyes of the HMD 100.

The beam splitter 275 may include a first beam splitter that can reflect the optical ray emitted from the display screen 270 and a second beam splitter that can reflect the optical ray emitted from the active element 240. The lens 280 (e.g., concave lens, convex lens, cylinder lens) may converge the optical ray reflected from the beam splitter 275. The active element 240 may reflect the optical ray emitted from the lens 280 by converging or diverging. The lens mirror 285 may converge the optical ray reflected from the beam splitter 275 and emit the optical ray to a user.

The polarizer 290 may include a plurality of polarizers (quarter wave plates, half wave plates). The prism 295 may broaden a field of view of a user. The prism 295 may be free curved prism that can expand the optical ray converged from the display screen 270 and induce to a user's eye.

Figure 3:
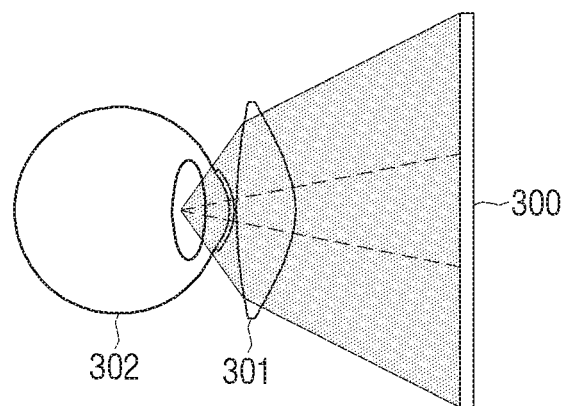
FIG. 3 is a diagram of an HMD that can correct the eyesight of a user according to the related art.

FIG. 3 is a diagram of an HMD that can correct the eyesight of a user according to the related art.

Referring to FIG. 3, in a related art, the user's eyesight may be corrected by disposing the lens mirror 301 constituting the optics of the HMD 100 and the display screen 300 on the uniform optical path and adjusting the distance between the lens mirror 301 and the display screen 300, i.e., the optical path length, to focus the image in the user's eye 302.

Further, in a related art, the user's eyesight may be corrected by disposing the display screen 300, the lens mirror 301, and a reflecting mirror (not illustrated) which configured the optics of HMD 100 on the uniform optical path and adjusting at least one of the first optical path from the display screen 300 to the reflecting mirror (not illustrated) and the second optical path from the reflecting mirror (not illustrated) to the lens mirror 301.

However, the above technology may have a problem in which the user's eyesight cannot be measured precisely and cannot be automatically corrected when a user of the HMD 100 is changed.

Figure 4:
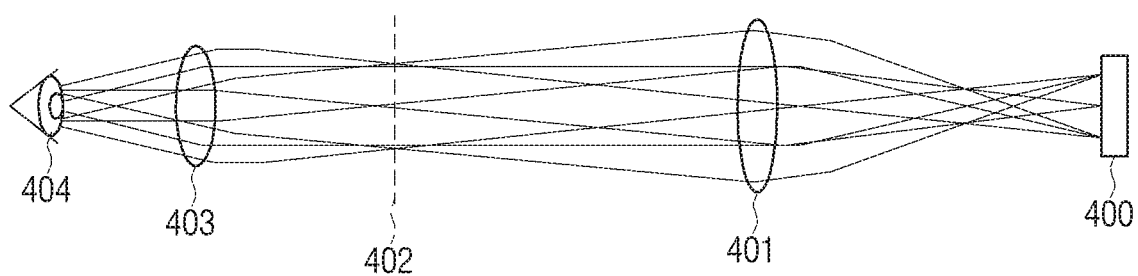
FIG. 4 is a diagram of a pupil forming design which is an optical design of an HMD according to an embodiment of the present disclosure.

FIG. 4 is a diagram of a pupil forming design which is an optical design of an HMD according to an embodiment of the present disclosure.

There are a non-pupil forming design and a pupil forming design as optical designs for the HMD 100. The non-pupil forming design can be easily established. Meanwhile, because the non-pupil forming design has a short path length, a short throw distance between the source image and the virtual reality image may be obtained. The short path length indicates that the display of HMD 100 is positioned near to the user's face and the user's eye. Such an optical design of the HMD 100 has a disadvantage in which modification is difficult to be established.

Meanwhile, the pupil forming design has a similar configuration to generating an image in a microscope, binoculars, or the periscope of a submarine.

Referring to FIG. 4, the pupil forming design may generate a medium image 402 of the source image transmitted to a first lens set 401 from the display 400. The generated medium image 402 may be relayed to the eye 404 of a user with a second lens set 403. The user's eye 404 may be positioned at the exit pupil area which is a virtual reality image.

The advantage of the pupil forming design may provide a desired path length from the image plane to the user's eye. Further, the pupil forming design may be implemented to provide a longer path length than the non-pupil forming design and move farther away from the user's face. Further, because the pupil forming design may include more lenses and mirrors, the optical correction can be enhanced.

Figure 5:
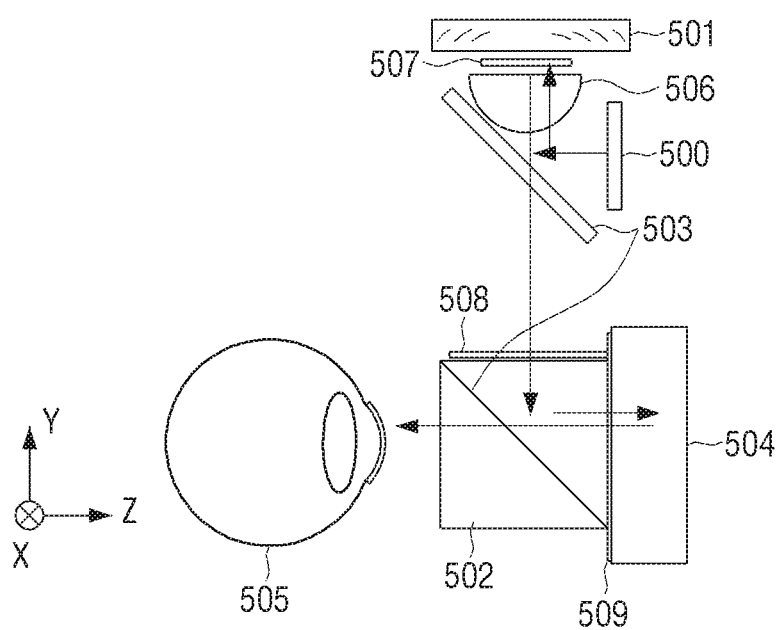
FIG. 5 is a diagram illustrating a detailed configuration of display optics of an HMD according to an embodiment of the present disclosure.

FIG. 5 is a diagram illustrating a detailed configuration of display optics of an HMD according to an embodiment of the present disclosure.

Referring to FIG. 5, the optics of the HMD 100 may include the display 500, the active element 501, the prism 502, the polarized beam splitter 503, the lens mirror 504, the lens 506, the first polarizer 507, the second polarizer 508, and a third polarizer 509.

The display 500 may be planar display or curved display. The display 500 may be a liquid display such as an LCD or a light emitting diode display such as an OLED.

The active element 501 may be implemented as a MEMS mirror including a plurality of the micro mirrors. The micro-mirrors comprise particles that may adjust the optical power and modify the mask pattern by rotating toward an X axis or a Y axis.

The HMD 100 may detect the user's eyesight with the mask pattern generated based on the varied optical power by controlling the gradient of at least some of the micro-mirrors in the active element 501. Further, the user's eyesight may be corrected by controlling the gradient of at least some of the micro-mirrors in the active element 501 based on the detected eyesight and adjusting a focal length of the image provided to the display.

Through the above process, the HMD 100 may measure and correct the user's eyesight more precisely. Further, the HMD 100 may reduce the tolerance with the precise eyesight measurement of the micro-mirror. A method for measuring the eyesight by varying the mask pattern of the active element 501 will be specifically explained by referring to FIGS. 7A to 7E.

The active element 501 may be arranged vertically to the optical path, and also arranged vertically to the display 500. The specific explanation regarding the configuration of the active element 501 will be explained below by referring to FIGS. 6A and 6B.

The prism 502 may broaden a field of view of a user. The polarized beam splitter 503 may play a role to separate the incident ray by penetrating or reflecting the light. The planar or the cube type beam splitter may be used.

The lens mirror 504 may be one of a concave lens mirror, a convex lens mirror, and a cylinder lens mirror. The lens 506 may include one or more of concave lenses, convex lenses, and cylinder lenses. The lens 506 and the lens mirror 504 may be configured as a single structure, or may be configured of a plurality of different lenses.

The first polarizer 507 and the third polarizer 509 may be composed of ¼ wave plates (quarter wave plates) while the second polarizer 508 may be composed of a ½ wave plate (half wave plate). ¼ wave plates 507, 509 and ½ wave plate 508 may generate various polarized states according to the states of the incident optical ray.

The display 500 may emit the optical ray and the first polarized beam splitter 503 arranged on the front face of the active element 501 may reflect the optical ray emitted by the display 500. The optical ray reflected by the first polarized beam splitter 503 may be converged on the lens 506, passed through ¼ wave plates, and converged on the active element 501.

The active element 501 may reflect the optical ray emitted from the lens 506 by converging or diverging. The optical ray emitted from the active element 501 may be passed through ¼ wave plates and converged on the lens 506. The light converged on the lens 506 may be passed through the first polarized beam splitter 503, passed through a ½ wave plate 508, reflected through the second polarized beam plate 503, passed through a ¼ wave plate 509, and entered the lens mirror 504. The lens mirror 504 may reflect the incident rays. The optical ray reflected from the lens mirror 504 may be passed through ¼ wave plate 509, passed through the second polarized beam splitter 503, and formed as an image on the user's retina 505.

Specifically, when the display 500 emits X polarized rays, X polarized rays may be reflected from the first polarized beam splitter and enter the active element 501. Herein, before entering the active element 501, X polarized rays may be passed through ¼ wave plate 507. The optical ray reflected from the active element 501 may be passed through ¼ wave plate 507 again, and Y polarized rays may be passed through the first polarized beam splitter 503.

Y polarized rays passed through the first polarized beam splitter 503 may generate a virtual reality image upon being incident on ½ wave plate 508, and Y polarized rays passed through ½ wave plate 508 may enter the lens mirror 504 as X polarized rays. The incident optical ray as X polarized rays may be passed through ¼ wave plate 509 twice (entered/reflected) and diverge Y polarized rays on the pupil 505 from the lens mirror 504.

Herein, according to an embedment of the pupil forming design, a user may view a virtual reality image on the exit pupil.

Figure 6A:
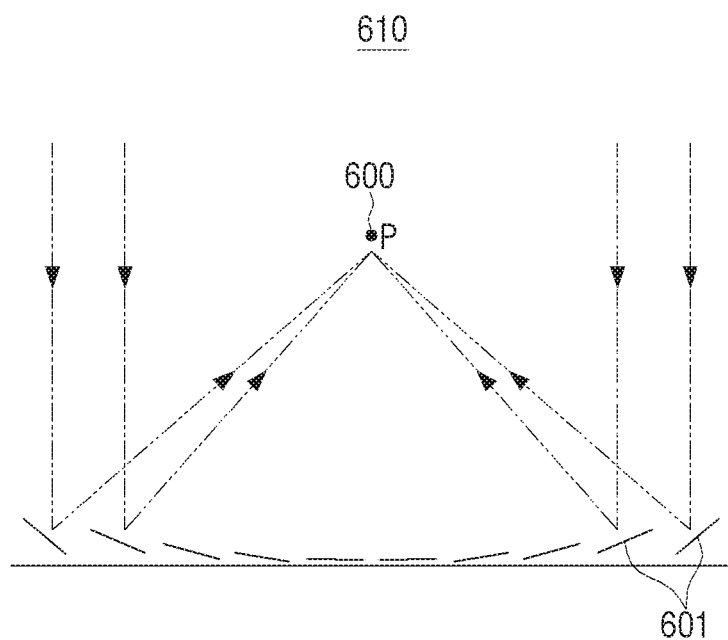
FIGS. 6A and 6B are diagrams of an active element constituting an HMD according to an embodiment of the present disclosure.
Figure 6B:
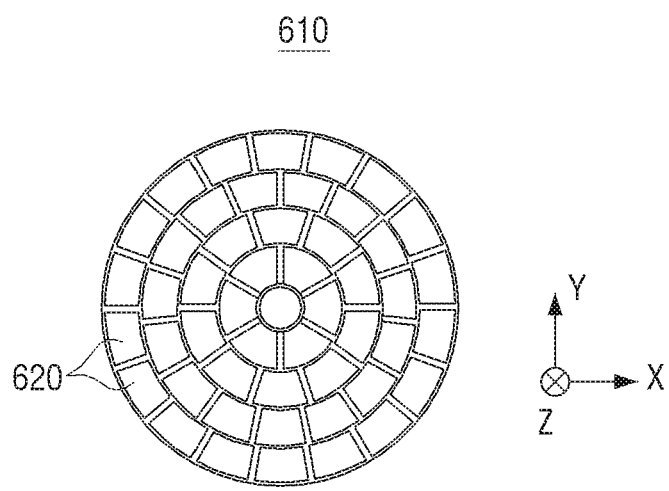

FIGS. 6A and 6B are diagrams of an active element constituting an HMD according to an embodiment of the present disclosure.

FIG. 6A is a diagram provided to explain that a MEMS mirror which is an active element forms an image according to an embodiment of the present disclosure.

Referring to FIG. 6A, MEMS mirror 610 may include a plurality of the micro-mirrors 601. MEMS mirror 610 may be controlled in terms of the position of the micro-mirror 601. The voluntarily dispersed optical ray may be converged on one point P 600 of the image plane.

FIG. 6B is a diagram illustrating a plane view of the MEMS mirror 610 which is an active element according to an embodiment of the present disclosure.

Referring to FIG. 6B, MEMS mirror 610 may be configured in the circular arrangement of the micro-mirrors 620, and the micro-mirrors 620 may have the uniform function to the mirror. The micro-mirrors 620 have a high reflecting degree. Each of the micro-mirrors 620 may have a fan shape to increase the reflective area that can enhance the optical efficiency. However, the circular arrangement and the fan shape are merely one of embodiments of the present disclosure for the explanation; the present disclosure is not limited to the above.

The lens (active element) having the MEMS mirror arrangement has the quickest response speed because the micro-mirrors 620 are of very small size and low mass. For example, the response speed of the micro-mirrors 620 may exceed 100 KHz. Thus, the changed speed of the focal length of the micro-mirrors 620 may be implemented to be greater than or equal to 100 KHz.

Further, the micro-mirrors 620 may be controlled so as to modify the focal length of the lens. The MEMS mirror 610 may control the translation or the rotation respectively regarding the micro-mirrors 620 in order to change the focal length. The rotation of the micro-mirrors 620 may change the direction of the optical ray toward the X axis and the Y axis, and the translation may adjust the phase of the optical ray toward the Z axis.

Thus, an embodiment of the present disclosure may be implemented such that the planar MEMS mirror 610 composed of a plurality of the micro-mirrors 620 may be arranged vertically with regard to the optical path of the HMD 100, and the specific optical ray for the eyesight measurement may be formed near to the center of the MEMS mirror 610. Through the above process, only the chief rays for the eyesight measurement among the optical ray emitted from the display may be formed as an image on the user's retina and the eyesight may be measured.

Further, the optical power may be adjusted by varying the focal length through the rotation and the translation of the micro-mirrors 620. The eyesight may be corrected through the above process.

FIGS. 7A to 7E are diagrams of a method for measuring the eyesight of a user by using an active element of an HMD according to an embodiment of the present disclosure.

Figure 7A:
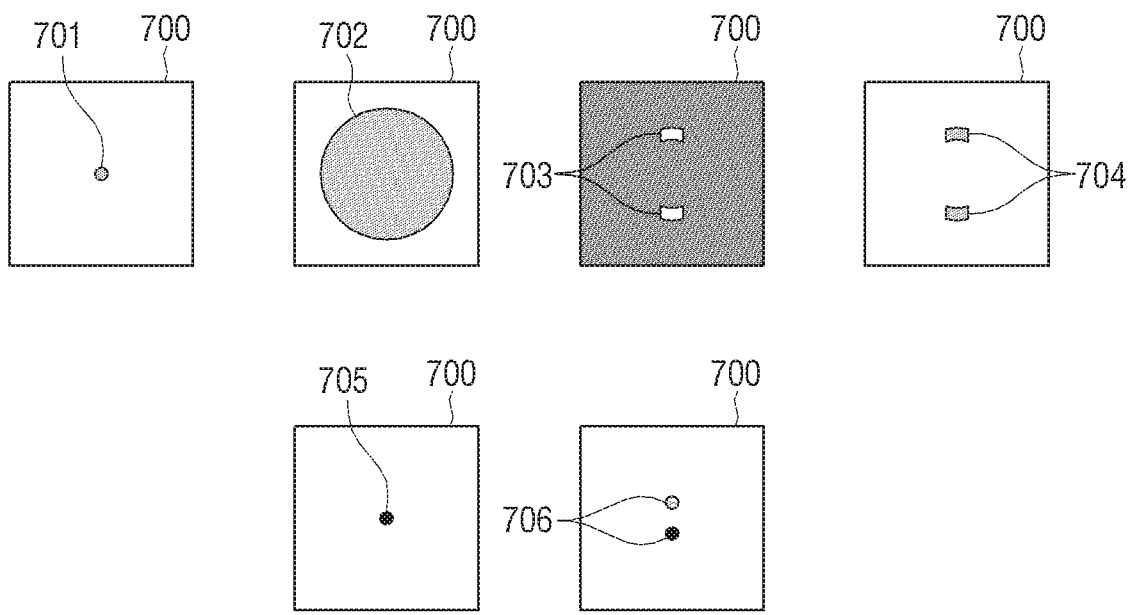
FIGS. 7A to 7E are diagrams of a method for measuring the eyesight of a user by using an active element of an HMD according to an embodiment of the present disclosure.

FIG. 7A is a diagram of mask pattern that is varied with an active element according to the eyesight of a user when the eyesight is measured by using optics.

Referring to FIG. 7A, when the display screen 700 emits the optical ray, a pixel 701 may be turned on in the display 700, and the spot-like pixel 701 which is turned on may enter the lens. When the optical ray emitted from the display screen 700 is passed through the lens, the size of the pixel 701 which is a spot-like optical ray may become an expanded spot-like optical ray with the lens. When the optical ray 702 passed through the lens enters the active element, only the specific optical ray may be masked near to the center of the active element with the rotation and the resonance of the micro-mirrors of the active element. Thus, a specific area optical ray 703 may be formed as an image on the active element among the spot-like the optical ray 702 passed through the lens. The specific area optical ray 703 formed as an image on the active element may be converged to the lens, and the other area optical ray may not penetrate through the lens. Thus, the optical ray passed through the active element may become the spot-like image 704 of the specific area which is previously formed on the active element.

According to Scheiner's principle which is the principle of the eyesight measurement, a general eyesight measuring method may measure the eyesight as the optical rays are focused on one point 705 regarding the normal eyesight, while the optical rays 706 are divided regarding myopia or hyperopia (farsightedness).

According to an embodiment of the present disclosure, by applying Scheiner's principle and using the active element, the HMD 100 may measure the eyesight by controlling the gradient of at least some of the micro-mirrors and driving the other optical ray to be away from the center such that only the optical ray for the eyesight measurement can be formed on the center of the retina.

The HMD 100 according to an embodiment of the present disclosure may passively perform the eyesight measurement by using the active element. Thus, the HMD 100 may be implemented to measure the user's eyesight by receiving a user command and varying the gradient of the micro-mirrors constituting the active element.

For example, the HMD 100 may be implemented to modify the gradient of the micro-mirrors constituting the active element by a user through a UI for the eyesight measurement or the menu button. Herein, the UI for the eyesight measurement or the menu button may be implemented within the HMD 100 or by an external device (e.g., a remote controller).

Specifically, a user may modify the gradient of the micro-mirrors constituting the active element while touching the screen of the HMD 100 or manipulating the menu button. A user may store the user's eyesight at the moment when the clear pattern is viewed from the HMD 100 while the gradient of the micro-mirrors constituting the active element is varied to the user's eyesight. The HMD 100 may be implemented to store the detected eyesight information based on the gradient information of the micro-mirrors constituting the active element and store the eyesight information with the user information (e.g., a user identifier (ID) and user's biometric information), when an eyesight storing command is input by a user. Herein, the user information may be user information previously stored in the HMD 100 by a user or information input together with the eyesight information by a user.

Figure 7B:
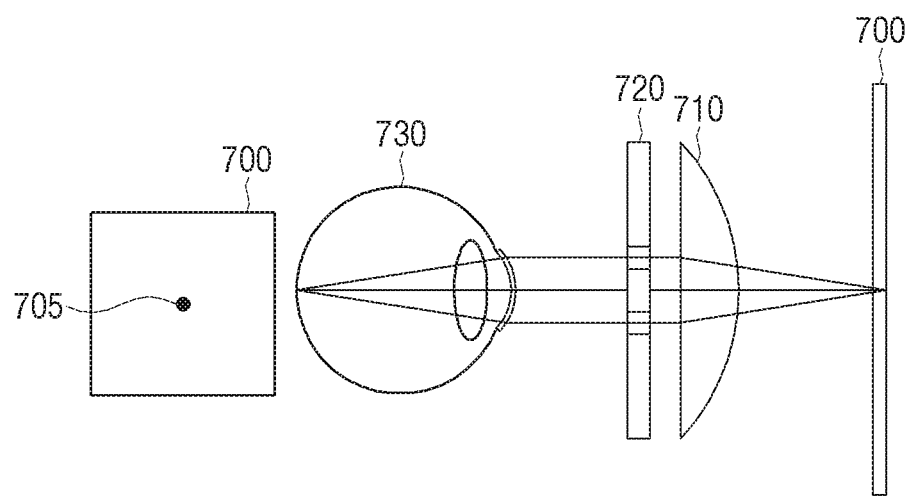
Figure 7C:
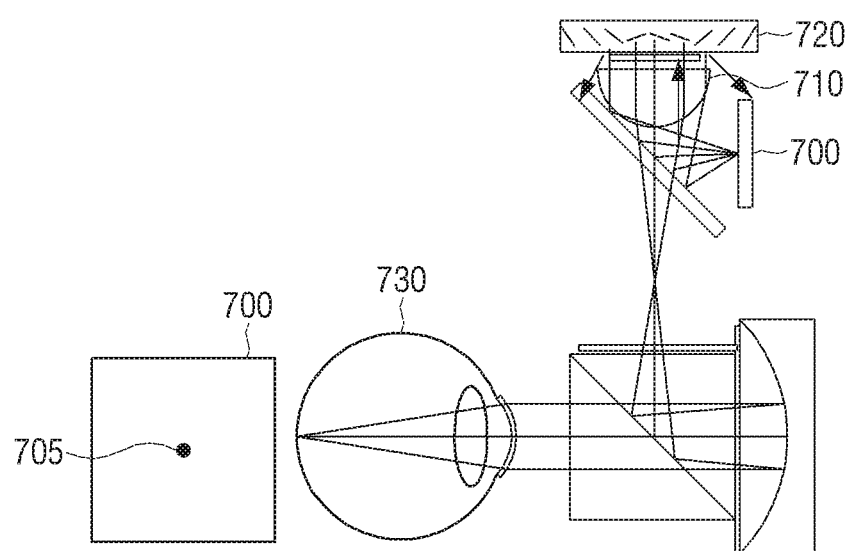

FIGS. 7B to 7E are diagrams of modification of the mask pattern with the active element when normal eyesight and hyperopia are measured. FIGS. 7B and 7C are diagrams illustrating the mask pattern with the active element when normal eyesight is measured.

Referring to FIGS. 7B and 7C, the spot-like optical ray 701 emitted from the display screen 700 which is explained in FIG. 7A may be expanded upon being passed through the lens 710. As described above in FIG. 7A, the optical ray passed through the lens may be expanded to spot-like image 702. The optical ray 702 diverged from the lens may enter the active element 720.

The optical ray 702 entering the active element 720 may modify the mask pattern by the translation and the rotation of the micro-mirrors constituting the active element 720. Accordingly, only the specific area optical ray according to the focal length of a user may be formed as an image on the active element 720.

As described in FIG. 7A, the optical ray formed on the active element may have the mask pattern 703 of the specific optical ray. Further, the optical ray after being passed through the active element may become the spot-like image 704 of the specific area which is previously formed on the active element. Referring to FIGS. 7B and 7C, the optical ray 704 passed through the active element 720 (see FIG. 7A) may be formed on the center of the user's retina 730, and the optical ray 705 for the user's eyesight measurement may be generated on the display screen 700. Thus, the eyesight can be measured.

Figure 7D:
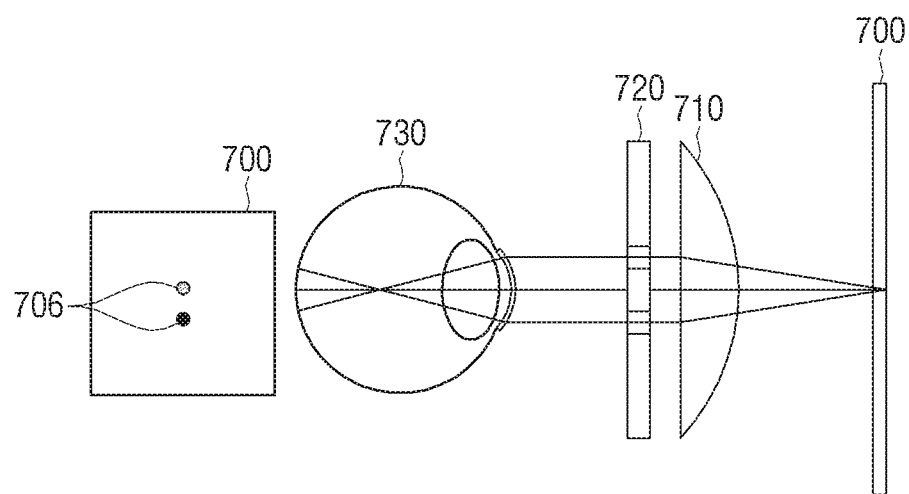
Figure 7E:
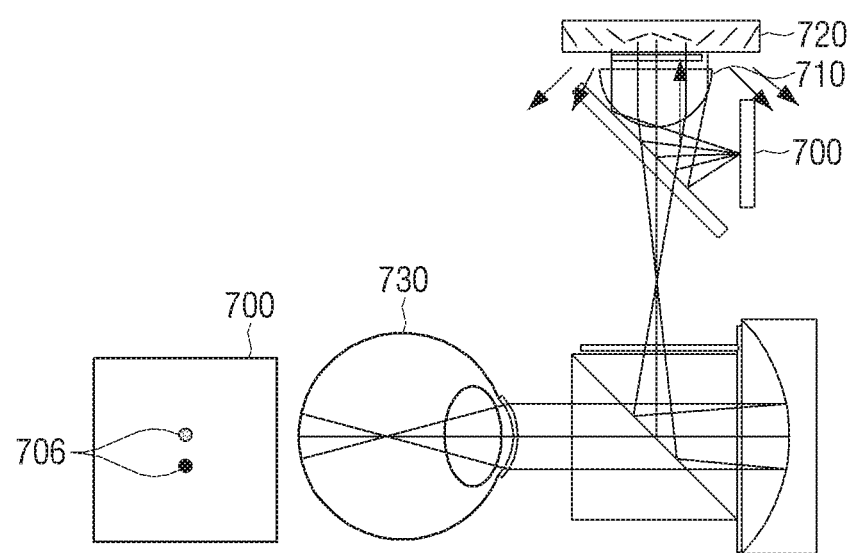

FIGS. 7D and 7E are diagrams illustrating the mask pattern with the active element when measuring myopia.

Referring to FIGS. 7D and 7E, the active element 720 may generate the different mask pattern from the normal eyesight (FIGS. 7B and 7C) by the rotation and the translation of the micro-mirrors constituting the active element 720 of the optical ray 702 converged on the lens 710. Herein, the optical ray 704 having the mask pattern formed and generated on the active element 720 may be formed on the front area of the user's retina 730 in FIGS. 7D and 7E, and the optical ray 706 for the user eyesight measurement may be separated and generated. Thus, myopia can be measured by using the above process. Further, astigmatism can be measured by adjusting the mask pattern generated with the rotation of the azimuth of the mask pattern generated by the active element 720.

As described above, the HMD 100 may control the display screen 700 to generate the optical ray for the eyesight measurement, control the active element 720 to form the optical ray for the eyesight measurement on the user retina 730 through the active element 720, and register the information of the active element 720 at the time point when an image is formed on the user retina 730 as user eyesight information.

Herein, the measured eyesight information may be stored in the memory of the HMD 100. The memory may store the user's biometric information together. For example, the user's biometric information may store various pieces of information such as iris recognition, voice recognition, face recognition, and fingerprint recognition. Thus, when a user uses the HMD 100 again, the HMD 100 may correct the eyesight automatically suitable for the user's eyesight information based on the user's biometric information.

Specifically, a user may select to execute the recognition through a user command, such as a UI providing user recognition menu, when the HMD 100 recognizes the user's biometric information or may automatically perform recognition when a user wears the HMD 100 on his head. When a user is recognized, the HMD 100 may correct the eyesight based on the user's eyesight information matched with the user's biometric information stored in the memory. As the technology to store and recognize the user's biometric information is applied to the HMD 100, the encrypting technology to protect the user information can be applied.

According to an embodiment of the present disclosure, the method for correcting the user eyesight in the HMD 100 may correct the user eyesight by adjusting the user optical power with the active element.

The optical power may indicate the lens power, and may be inversely proportional to the focal length. Thus, the HMD 100 may have the different focal lengths according to the user eyesight. The active element composed of a plurality of the micro-mirrors may control the different focal lengths represented based on the user eyesight. As illustrated in FIG. 6A, the active element including MEMS mirrors may modify the direction of the optical ray with the rotation of the micro-mirrors, adjust the phase of the optical ray with the translation, and modify the focal length of the active element. Thus, the eyesight can be corrected.

Further, according to an embodiment of the present disclosure, the HMD 100 can reduce eye fatigue by varying the focal point of the virtual reality image. When the HMD 100 is used for a long time, the focal length of the virtual reality image may be fixed on one position. Herein, eye fatigue may occur because the focal point is placed on one position for a long time, and eyesight loss may occur.

In order to solve the above problem, the HMD 100 may modify the focal point of the virtual reality image voluntarily at a designated time by controlling the active element. Thus, the HMD 100 may adjust the focal point of the virtual reality image by adjusting the optical power of the active element at a specific time. Further, the HMD 100 may modify the focal point of the virtual reality image by estimating the object position displayed on the display screen and applying the image recognition technology. Herein, eye fatigue can be reduced by matching the focal point of the virtual reality image on the position of the ambient object with the active element.

According to an embodiment of the present disclosure, when the eyesight of a myopic user is 3 diopters, the virtual reality object may be formed by 33 cm distance. Herein, when applying a 3 diopters disparity which is uniform to the object distance at infinity represented from normal eyesight, a myopic user may feel dizziness. Incidentally, a diopter is a unit of measurement of the optical power of a lens or curved mirror, which is equal to the reciprocal of the focal length measured in meters (that is, 1/meters). Thus, an embodiment of the present disclosure may be implemented that the optimized value of the image distortion may be applied by providing the image in which the disparity is adjusted to be suitable for the user's eyesight.

Further, according to an embodiment of the present disclosure, the HMD 100 may correct a high aberration. Because the whole area of the eye cannot be measured in the corrective lenses, only a low aberration can be corrected. However, the active element may be composed of a plurality of MEMS mirrors and the focal lengths respectively regarding areas of the micro-mirrors may be adjusted, which approximate the different lens powers. Thus, the correcting a high aberration can be performed. Through the above process, a high aberration may be detected by applying the high aberration detecting technology implemented to measure the whole area of the eye (full aberration "finger print" of the eye), and the detected aberration may be corrected by using the active element.

Further, according to an embodiment of the present disclosure, the HMD 100 may expand an eyesight adjustment range by establishing offset values on the lens power of the lens mirrors constituting the optics. For example, regarding a plurality of MEMS mirrors constituting the active element, a chromatic aberration increases with the diffraction when the optical power increases. Thus, the HMD 100 should be driven with a low optical power in order to reduce the chromatic aberration. Because the optical power is inversely proportional to the focal length, the optical power may have a low value when the focal length is large.

In order to increase the focal length in the HMD 100, the optical power offset may be established on the lens mirror, and the optical power of the offset value established in the lens mirror may be subtracted in the active element.

For example, when the eyesight of a normal user is 60 diopters and when the optical power of the lens mirror is 27 diopters, the optical power that can be used by MEMS mirrors of the active element may be assumed to be from +3 diopters to −3 diopters. When an offset value of the optical power is not established on the lens mirror and when normal eyesight is measured, the lens mirror may have the optical power of 27 diopters and the MEMS mirrors may have the optical power of from +3 diopters to −3 diopters. Herein, when myopia is measured, the lens mirror may have the optical power of 27 diopters and the MEMS mirrors may correct the eyesight from 0 diopters to −3 diopters.

Meanwhile, according to an embodiment of the present disclosure, when an offset value of the optical power is established on the lens mirror and when normal eyesight is measured, the lens mirror may have the optical power of 24 diopters (27 diopters−3 diopters) and the MEMS mirrors may have the optical power from 0 diopters to −6 diopters. Thus, when myopia is measured, the eyesight to −6 diopters can be measured and corrected.

The above is merely one of embodiments of the present disclosure for the explanation, and accordingly the embodiments of the present disclosure can be applied and varied by varying the optical power, measuring and correcting the eyesight through various methods and technologies.

Figure 8A:
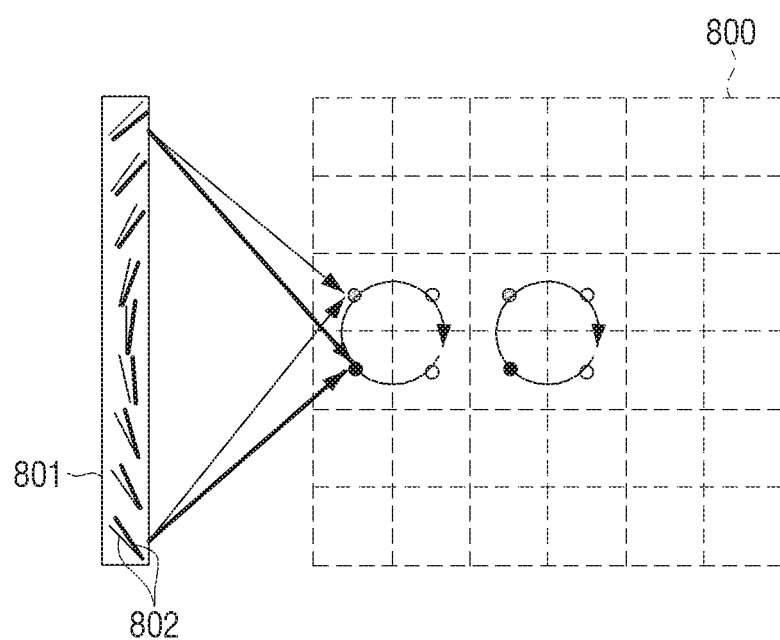
FIGS. 8A and 8B are diagrams of a high definition display implemented with a high-speed tilting of the active element of an HMD according to an embodiment of the present disclosure.
Figure 8B:
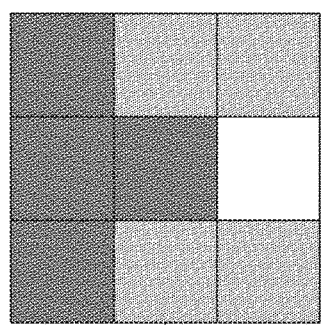
Figure 8B:
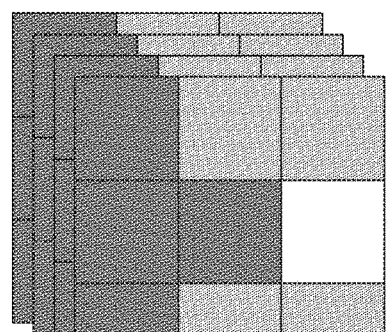
Figure 8B:
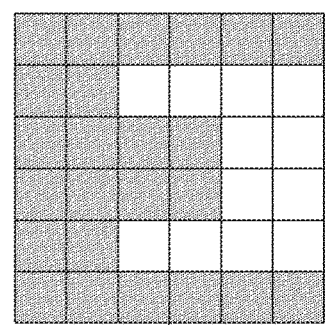

FIGS. 8A and 8B are diagrams of a high definition display implemented with a high-speed tilting of the active element of an HMD according to an embodiment of the present disclosure.

The angular resolution of the normal human eye is 1/60 arcmin. Thus, the human eye can distinguish 60 pixels per 1 arcmin. The arcmin indicates an angle of one pixel; as an arcmin value becomes smaller, the resolution becomes higher. A current HMD for the virtual reality is about 15 pixel/degree. Thus, when viewing an image with the HMD 100, dots may be viewed on the pixels, deteriorating the immersion.

FIG. 8A is a diagram of the high-speed driving of the active element composed of MEMS mirrors.

Referring to FIG. 8A, effects of approximately doubled resolution may be obtained by high-speed driving a plurality of the micro-mirrors 802 of the active element 801 toward the tilts of the X axis direction and the Y axis direction. As described in FIG. 6B, because the active element having the arrangement of MEMS mirrors includes very light and small micro-mirrors 620 (low mass), the quickest response speed may be obtained. For example, the response speed of the micro-mirrors 620 may exceed 100 KHz. Thus, the change speed of the focal length of the micro-mirrors 620 may be greater than or equal to 100 KHz.

For example, as illustrated in FIG. 8A, when the micro-mirrors 802 are driven at 120 KHz, the focal point of the active element 801 may be shaken on the focal point plane toward the left and the right direction (X direction, Y direction) with a high speed. Accordingly, uniform low resolution screens on the left and the right of the display 800 may be combined, and the effects can be obtained in which a high resolution image may be displayed according to the afterimage effect.

Specifically, referring to FIG. 8B, one pixel may have 10 micrometers and the display may include 3×3 pixels. For example, when the field of view of 50 degrees is implemented by using a 1,000×1,000 display (10 micrometer pixel), each resolution 810 may be about 1,000/30 pixels/degree, i.e., about 33 pixels/degree.

According to an embodiment of the present disclosure, the HMD 100 may be high-speed driven so as to draw a circle of 5 micrometers, which is half of each pixel, by using the active element 801 illustrated in FIG. 8A regarding each pixel of 3×3 pixel low resolution display 810 illustrated in FIG. 8B. Herein, the display of the HMD 100 may be synchronized with the position of each pixel, a plurality of the low resolution image 820 may be scanned, and the uniform low resolution screens may be combined with each other and displayed. Herein, the HMD 100 may be implemented such that a plurality of the combined low resolution screens 820 can become high resolution images 830 respectively having the resolution of about 60 pixels/degree according to the afterimage effect.

Figure 9A:
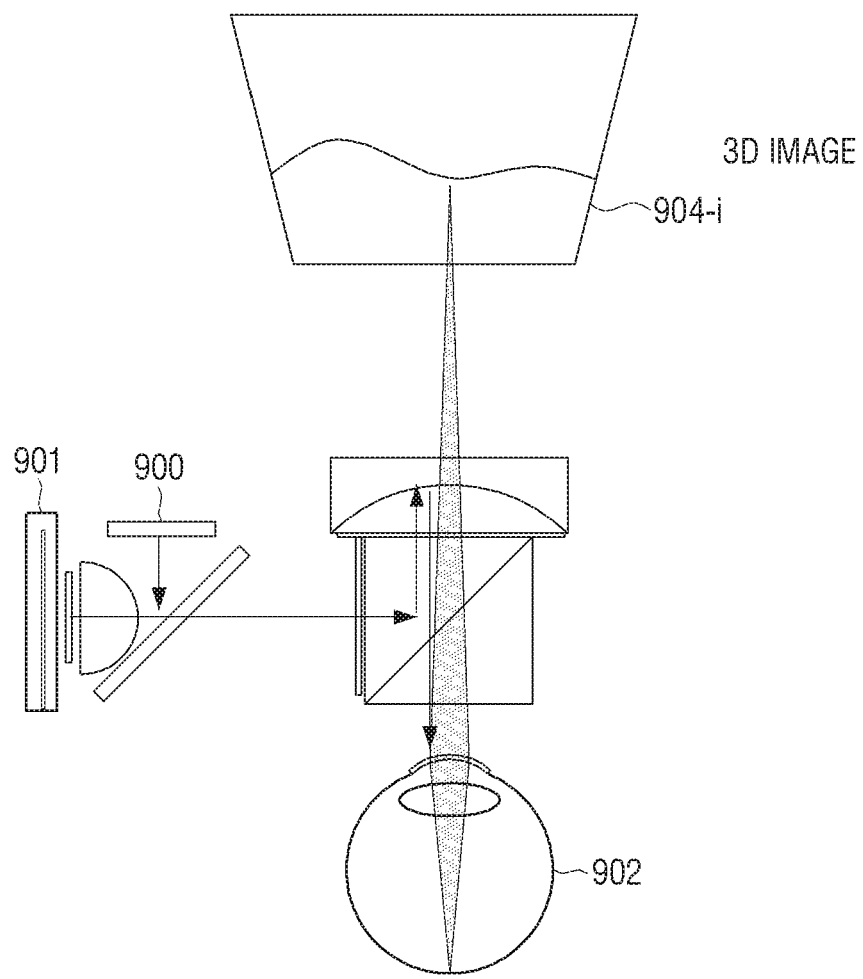
FIGS. 9A to 9C are diagrams of an HMD that controls the visual accommodation/convergence of one eye by controlling a focal point of a virtual reality image with an active element according to an embodiment of the present disclosure.
Figure 9B:
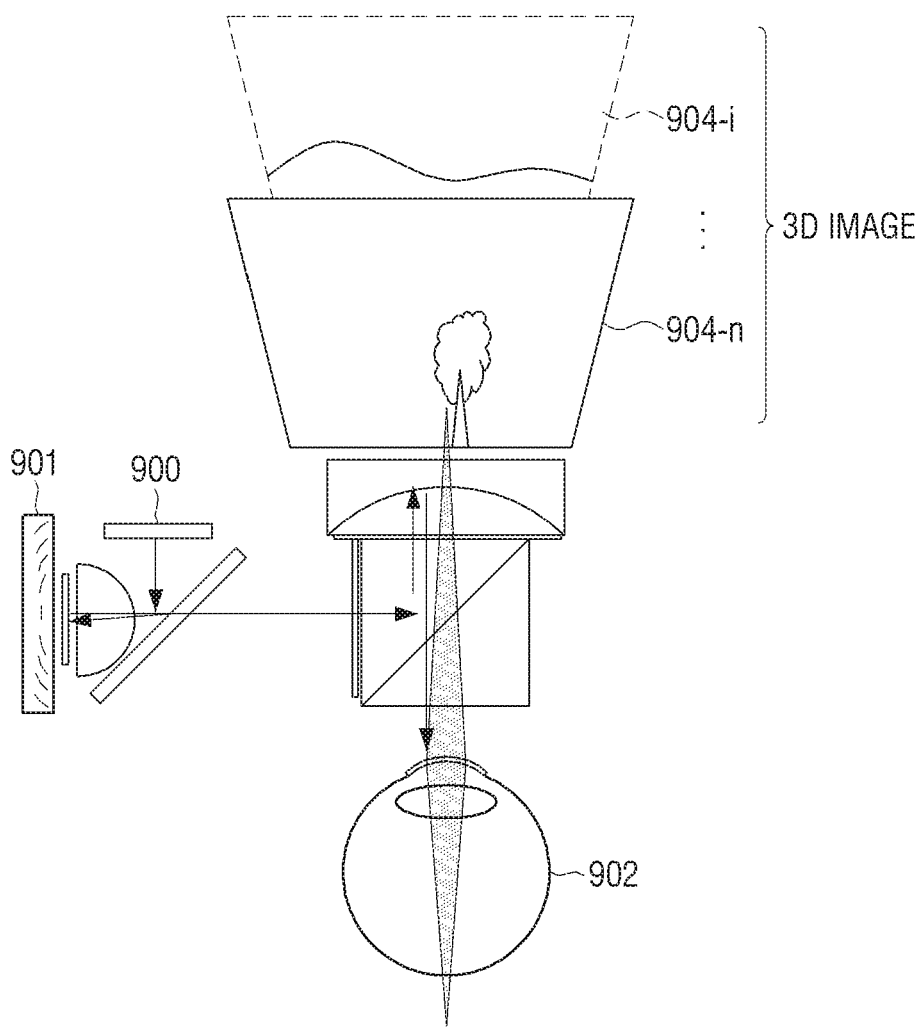
Figure 9C:
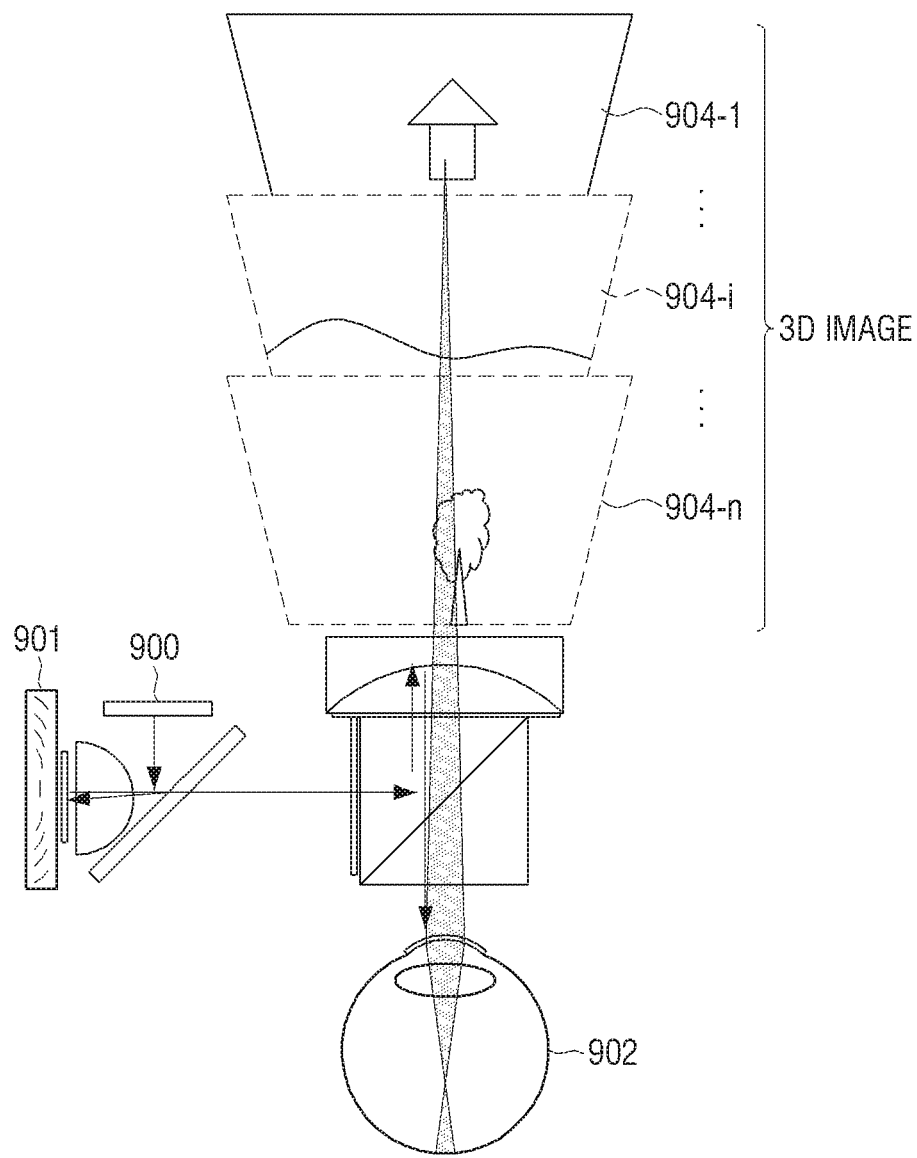

FIGS. 9A to 9C are diagrams of an HMD that controls the visual accommodation/convergence of one eye by controlling a focal point of a virtual reality image with an active element according to an embodiment of the present disclosure.

The HMD 100 may modify the focal point of the virtual reality image displayed on the display at a designated time.

Referring to FIGS. 9A to 9C, a focal point of a layer 904-*i* respectively regarding 3D images may be adjusted by time-sharing driving the optical power of MEMS mirrors in the active element.

Further, the HMD 100 may estimate the object position within the virtual reality image from the virtual reality image displayed on the display screen 900 according to the image recognition method. Herein, the HMD 100 may adjust a focal length of the virtual reality image by varying a focal point of the image with the active element based on the estimated object position. Further, the HMD 100 may adjust a focal point of a layer of the virtual reality image by varying the power of the active element 901 proportionally to the distance from the user's eye 902 to the object within the virtual reality image.

For example, FIG. 9A is a diagram of the optical power of the active element 901 that is adjusted when a user views the virtual reality image through the HMD 100 on a designated distance 904-*i* at which the object is placed from the eye 902. There is no change in the tilt of the micro-mirrors constituting the active element 901 when viewing the object on the designated distance 904-*i*.

Referring to FIG. 9B, when there is a virtual reality layer 904-*n* in which the object is placed nearer to the eye than the designated distance 904-*i*, MEMS mirrors of the active element 901 may be changed in terms of the tilt according to the focal length of the object respectively within the images, which adjust the optical power to be +diopter.

Referring to FIG. 9C, when there is a virtual reality layer 904-1 in which the object is placed farther from the eye than the designated distance 904-*i*, MEMS mirrors of the active element 901 may be changed in terms of the tile according to the focal length of the object respectively within the images, which adjusting the optical power to be −diopter.

Thus, when viewing the virtual reality image, the HMD 100 may establish a designated value (e.g., 1 m) of the distance from the user's eye to the object within the virtual reality image to be a threshold. According to the established standard, the HMD 100 may time-sharing modify the focal length with the optical power of −diopter in a 3D layer in which the object is farther from the eye than 1 m. Further, the HMD 100 may time-sharing modify the focal length with the optical power of +diopter in the 3D layer in which the object is placed nearer to the eye than 1 m.

Herein, the 3D layer farther than the threshold distance may follow the principle of correcting myopia. Further, the 3D layer much farther than the threshold distance may lead to the effects in which a two-dimensional (2D) image 905 is viewed.

Specifically, a number of 3D layers may be divided, for example, into 16, and one 3D image may be created, for example, on a 30 Hz basis. In the MEMS device of 10 KHz, MEMS mirrors of the active element may then be configured to be driven at 30×16=480 Hz.

Figure 10A:
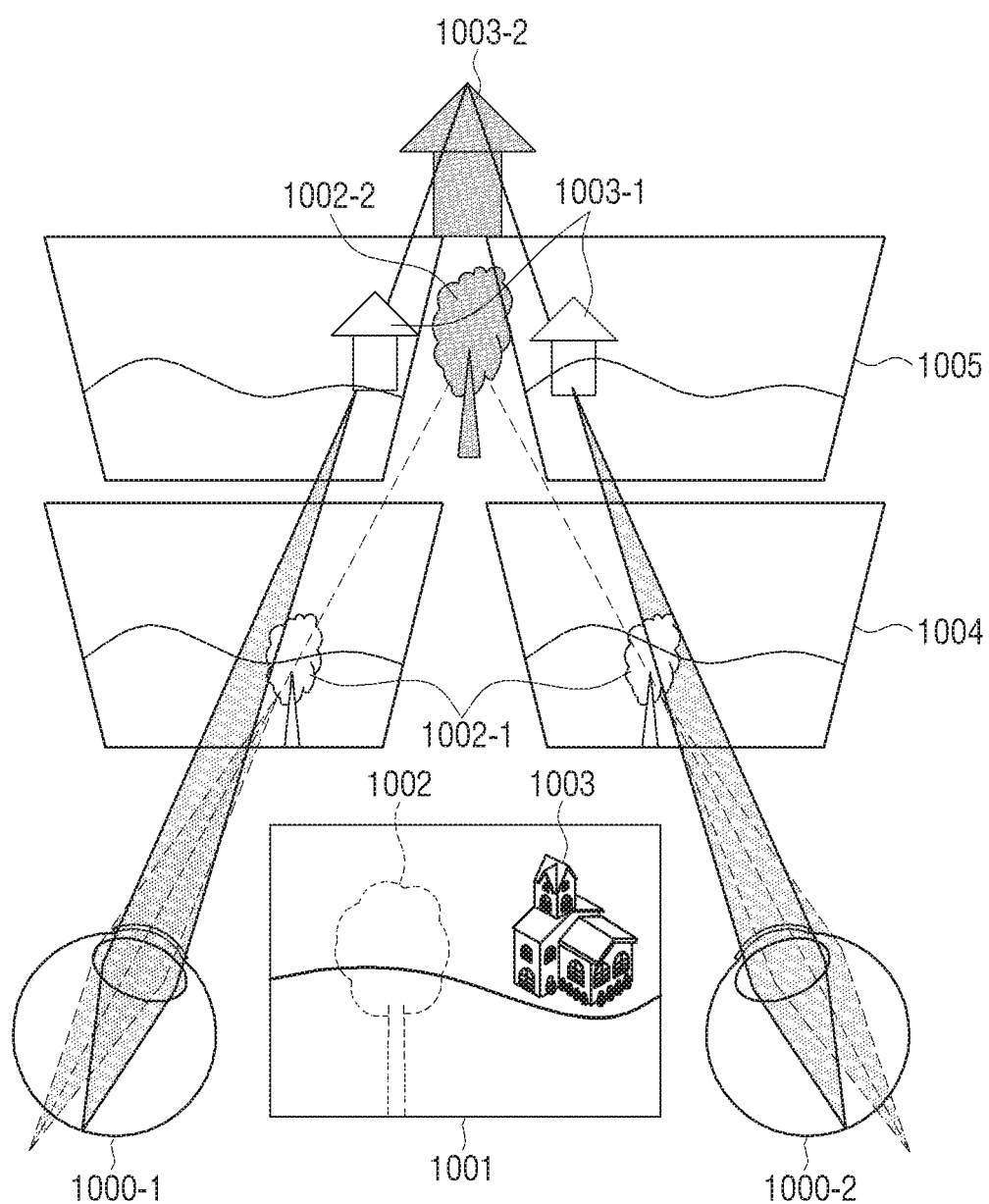
FIGS. 10A and 10B are diagrams of an HMD that performs a visual accommodation/convergence according to a distance of a virtual reality image with an active element according to an embodiment of the present disclosure.
Figure 10B:
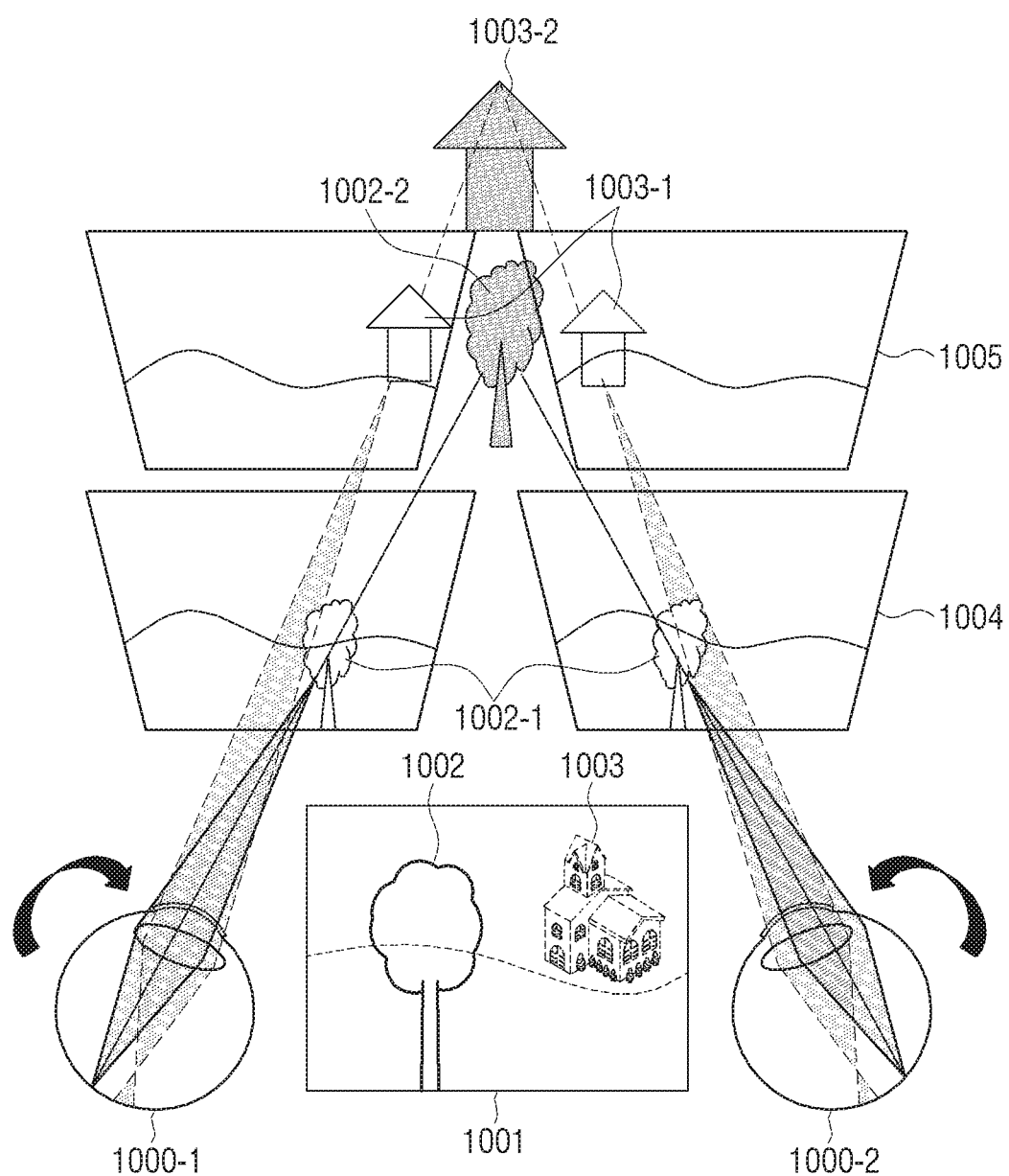

FIGS. 10A and 10B are diagrams provided to explain that the HMD 100 performs the visual accommodation and the visual convergence of the two eyes with the active element according to the distance of the virtual reality image according to an embodiment of the present disclosure.

As described in FIGS. 9A to 9C, the HMD 100 may adjust a focal point of a layer respectively regarding 3D images by time-sharing driving the optical power of MEMS mirrors in the active element 901.

FIGS. 10A and 10B are diagrams of an HMD that performs a visual accommodation/convergence according to a distance of a virtual reality image with an active element according to an embodiment of the present disclosure.

Referring to FIG. 10A, the HMD 100 can reduce eye fatigue because the visual accommodation and the visual convergence of the two eyes 1000-1, 1000-2 may be adjusted to the object 1003 placed on a longer distance among the objects 1002, 1003 within the virtual reality image 1001.

The virtual reality image 1001 may include the objects 1002, 1003. The HMD 100 may estimate an object's position within the virtual reality image displayed on the display with image recognition technology. Thus, the HMD 100 may estimate the object 1002-1 placed on a nearer distance to the eye and the object 1003-1 placed on a longer distance from the user eye among the objects 1002, 1003.

When there is a virtual reality image layer 1004 in which the object 1002-1 is placed nearer to the eye, MEMS mirrors of the active element 901 may be changed in terms of the tilt according to the focal length of the object 1002-1 within the image, which adjust the optical power to be +diopter, as described in FIG. 9B. Thus, eye fatigue can be reduced because the visual accommodation and the visual convergence of the user's eye 1000-1 are fit to the object 1002-2 placed on a nearer distance.

Referring to FIG. 10B, the HMD 100 may reduce eye fatigue because the visual accommodation and the visual convergence of the two eyes 1000-1, 1000-2 are fit to the object 1002 on the nearer distance among the objects 1002, 1003 within the virtual reality image.

The virtual reality image 1001 may include the objects 1002, 1003. The HMD 100 may estimate the object position within the virtual reality image displayed on the display with the image recognition technology. Thus, the HMD 100 may estimate the object 1002-1 on the nearer distance to the eye and the object 1003-1 on the longer distance from the user eye among the objects 1002, 1003.

When there is a virtual reality image layer 1005 in which the object 1003-1 is placed on a longer distance from the eye, MEMS mirrors of the active element 901 may be changed in terms of the tilt according to the focal length of the object 1003-1 within the image, which adjusting the optical power to be −diopter, as described in FIG. 9C. Further, the eye fatigue may be reduced because the visual accommodation and the visual convergence of the user eyes 1000-1, 1000-2 are fit to the object 1003-2 placed on the longer distance.

Through the above method, the HMD 100 may minimize eye fatigue by varying a focal point of a user when a designated time is passed. Thus, when the focal length between the user's eye and the HMD 100 image is a longer distance and when a user views the image for more than a designated time, the HMD 100 may move a focal point of a user to the object in which a focal length is placed on the nearer distance among the objects within the image. Meanwhile, when a focal length between the user's eye and the HMD 100 image is a nearer distance and when the user views the image for more than the designated time, the HMD 100 may move the focal point of the user to the object in which the focal length is placed on a longer distance among the objects within the image.

Figure 11:
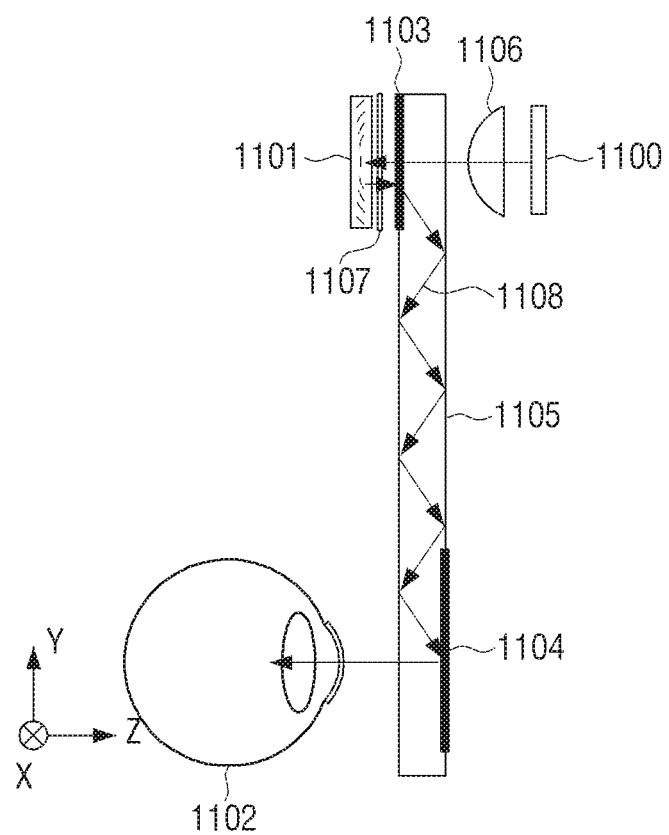
FIG. 11 is a diagram illustrating configuration of an HMD for an augmented reality image which uses an active element and a diffraction element according to an embodiment of the present disclosure.

FIG. 11 is a diagram illustrating configuration of an HMD for an augmented reality image which uses an active element and a diffraction element according to an embodiment of the present disclosure.

The augmented reality is technology to combine the virtual reality image with the physical environmental dimension of the real world. Herein, a problem may occur in which focal points between the virtual reality image and the reality image are not consistent.

Referring to FIG. 11, an X polarized optical ray emitted from the display screen 1100 may pass through the lens 1106, penetrate through the first diffraction element 1103, pass through ¼ wave plate 1107, and converge on the active element 1101. Herein, the lens 1106 may be implemented as a collimating lens to generate the X-polarized optical ray to be a parallel optical ray.

The first diffraction element 1103 may be arranged on an internal area of a light guide 1105 and in parallel with the active element 1101. Further, the first diffraction element 1103 may pass the X-polarized optical ray which is first a linear polarized optical ray emitted from the display 1100, and diffract a Y-polarized optical ray which is a second linear polarized optical ray vertically with respect to the first linear polarized optical ray.

The active element 1101 may adjust the gradient with the rotation and the translation of the micro-mirrors. The user's eyesight may be measured with the modifiable masking pattern of the active element 1101. Further, the active element 1101 may correct the user's eyesight by adjusting the optical power.

The active element 1101 may modify an angle of the optical ray 1108 by diverging the Y-polarized optical ray with the ¼ wave plate 1107 and total-reflecting on the first diffraction element 1103. Herein, the first diffraction element 1103 and the second diffraction element 1104 may be arranged on the internal area of the light guide 1105, and the light guide may be a waveguide which is planar glass. The optical ray 1108 diffracted by the first diffraction element 1103 may be total-reflected within the light guide 1105, and diffracted on the second diffraction element 1104. The optical ray 1108 diffracted on the second diffraction element 1104 may be formed as an image on the user's retina 1102.

Herein, the optical axis of the active element 1101 may be placed near to the range from 0 degrees to +/−15 degrees regarding the eye optical axis, Z axis, on the exit pupil axis. Accordingly, the HMD 100 may be established to improve the focal point inconsistency between the virtual reality image and the reality image while being manufactured in a form of thin glasses by disposing the active element on the side surface so as not to obstruct the front visual field of the eye 1102.

The above X polarized and Y polarized optical ray are merely one of embodiments of the present disclosure for the explanation; the present disclosure is not limited to the above, and other various modifications can be implemented.

Figure 12:
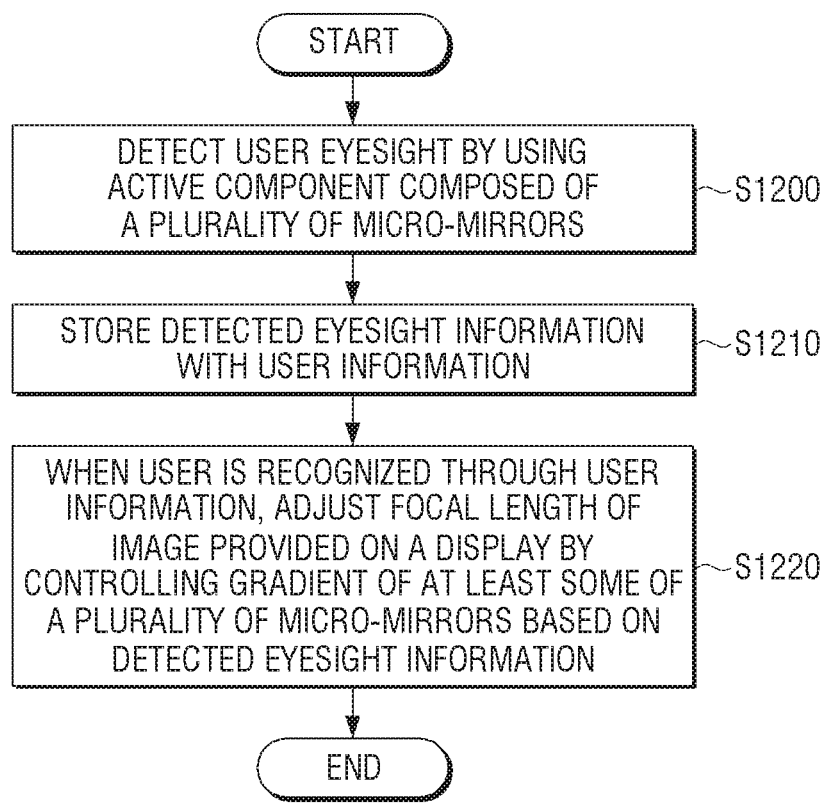
FIG. 12 is a flowchart of a method for measuring and correcting the eyesight of a user by using an active element of an HMD according to an embodiment of the present disclosure.

FIG. 12 is a flowchart of a method for measuring and correcting the eyesight of a user by using an active element of an HMD according to an embodiment of the present disclosure.

At operation S1200, the HMD 100 may detect the user's eyesight by using the active element composed of a plurality of the micro-mirrors. The method for detecting the eyesight is specifically explained above, and will not be further described below.

At operation S1210, the HMD 100 may store the detected user's eyesight information with the user's biometric information. For example, the user's biometric information may include various pieces of information such as iris recognition, voice recognition, face recognition, and fingerprint recognition. Thus, when a user reuses the HMD 100, the HMD 100 may correct the eyesight suitable for the user's eyesight information automatically based on the user's biometric information.

At operation S1220, when recognizing a user based on the stored user information, the HMD 100 may adjust a focal length of the image provided to the display by controlling the gradient of at least some of a plurality of the micro-mirrors based on the detected eyesight information. The method for adjusting a focal length is already described above, and will not be further explained below.

As described above, the HMD apparatus according to the embodiments of the present disclosure may provide an optimized image to a user by measuring and correcting the user's eyesight with an active element. Further, the HMD apparatus may be miniaturized by using the active element, and provide a high definition display screen to a user.

Further, a program to perform the above described control method may be stored in various recording media in addition to a storage (not illustrated), and provided with the display apparatus.

For example, a non-transitory computer readable medium storing the program which performs the method through the processor (not illustrated) of the display apparatus may be provided.

Specifically, the above various applications or programs may be stored and provided in non-transitory computer readable recording medium such as compact disc (CD), digital versatile disc (DVD), hard disk, Blu-ray disk, USB, memory card, or ROM, but the present disclosure is not limited thereto.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A head mounted display, the head mounted display comprising:
    a display configured to emit an X-polarized ray;
    a lens for making the X-polarized ray emitted from the display a parallel ray;
    a first diffraction element for transmitting or diffracting a ray received from the lens;
    a quarter wave plate for transmitting the parallel ray transmitted from the first diffraction element;
    an active element configured to converge the parallel ray that passed through the quarter wave plate and diverge the ray;
    a light guide plate through which the ray diverged from the active element and the ray diffracted at the first diffraction element pass; and
    a second diffraction element for diffracting the ray that passed through the light guide plate and forming an image on a user's retina.

2. The head mounted display of claim 1, wherein the lens is a collimating lens.

3. The head mounted display of claim 1, wherein the first diffraction element is disposed to be parallel with the active element.

4. The head mounted display of claim 1, wherein the first diffraction element and the second diffraction element are disposed inside the light guide plate.

5. The head mounted display of claim 4, wherein the first diffraction element transmits the X-polarized ray in the parallel ray, and diffracts a Y-polarized ray in the parallel ray.

6. The head mounted display of claim 1,
    wherein the active element comprises a micro-mirror, and
    wherein optical power can be adjusted and a mask pattern can be varied by adjusting a tilt of the micro-mirror by a rotation movement and a translational movement of the micro-mirror.

7. The head mounted display of claim 1,
    wherein the active element diverges a Y-polarized ray that passed through the quarter wave plate, and
    wherein the first diffraction element totally reflects the Y-polarized ray, and modifies an angle of the ray.

8. The head mounted display of claim 1, wherein the light guide plate is a wave guide which is planar glass.

* * * * *